United States Patent [19]

Rickwood et al.

[11] Patent Number: 5,833,885
[45] Date of Patent: Nov. 10, 1998

[54] PHOTOCHROMIC COMPOUNDS

[75] Inventors: Martin Rickwood, Southport; Sean Derek Marsden, St. Helens, both of United Kingdom

[73] Assignee: Pilkington PLC, St. Helens, United Kingdom

[21] Appl. No.: 772,466

[22] Filed: Dec. 23, 1996

Related U.S. Application Data

[63] Continuation of Ser. No. 612,080, Mar. 7, 1996, abandoned, which is a continuation of Ser. No. 284,232, Aug. 2, 1994, abandoned.

[30] Foreign Application Priority Data

Aug. 13, 1993 [GB] United Kingdom .................... 9316890

[51] Int. Cl.$^6$ .......................... G02B 5/23; C07D 265/00
[52] U.S. Cl. .......................... 252/586; 544/71; 540/466; 540/543
[58] Field of Search .............................. 252/586; 544/71, 544/6; 540/466, 543

[56] References Cited

U.S. PATENT DOCUMENTS

| | | | |
|---|---|---|---|
| 4,980,089 | 12/1990 | Heller ........................................ | 252/586 |
| 4,986,934 | 1/1991 | Kwiatkowski et al. .................. | 252/586 |
| 5,066,818 | 11/1991 | Gemert et al. ........................... | 549/389 |
| 5,106,998 | 4/1992 | Tanaka et al. ............................ | 549/331 |
| 5,114,621 | 5/1992 | Guglielmetti ............................ | 252/586 |
| 5,266,447 | 11/1993 | Takahashi et al. ....................... | 252/586 |
| 5,330,686 | 7/1994 | Smith et al. .............................. | 252/586 |
| 5,340,857 | 8/1994 | Van Gemert ............................. | 524/110 |

FOREIGN PATENT DOCUMENTS

| | | |
|---|---|---|
| 0 245 020 B1 | 11/1987 | European Pat. Off. . |
| 0 246 114 | 11/1987 | European Pat. Off. . |
| 0 350 009 A1 | 1/1990 | European Pat. Off. . |
| 0 358 774 A1 | 3/1990 | European Pat. Off. . |
| 358774 | 3/1990 | European Pat. Off. . |
| 0 401 958 A2 | 12/1990 | European Pat. Off. . |
| 0 402 228 A3 | 12/1990 | European Pat. Off. . |
| 0 489 655 A1 | 6/1992 | European Pat. Off. . |
| 0 562 915 A1 | 9/1993 | European Pat. Off. . |
| 0 600 668 A1 | 6/1994 | European Pat. Off. . |
| 2 200 908 | 8/1988 | United Kingdom . |
| WO 88/02371 | 4/1988 | WIPO . |
| WO 90/07507 | 7/1990 | WIPO . |
| WO 92/01959 | 2/1992 | WIPO . |
| WO 92/09593 | 6/1992 | WIPO . |
| WO 93/10112 | 5/1993 | WIPO . |
| WO 93/17071 | 9/1993 | WIPO . |

OTHER PUBLICATIONS

K. Yamamoto et al., Chemical Abstracts, vol. 116, No. 12, Abstract No. 116688y, Mar. 23, 1992, p. 710.
S. Yamamoto et al., Chemical Abstracts, vol. 116, No. 4, Abstract No. 31510j, Jan. 27, 1992, p. 722.
Ya. N. Malkin et al., "Quantitative Study of the Photostability of Spiropyrans," J. Photochem. Photobiol. A, vol. 49, No. 1–2, 1989, pp. 75–88.
Ya. N. Malkin et al., "Quantitative Study of the Photostability of Spiropyrans," vol. 39, No. 2, 1990, pp. 236–242.

T. B. Krasieva et al., "Photochemistry of Spiropyrans of the Dithiolane Series With Polycondensed Chromene Fragments," vol. 38, No. 11, 1989, pp. 2297–2302.
Vijaya Kumar et al., *Glycomaurin and Glycomaurrol, New Carbazole Alkaloids from Glycosmis mauritiana (Rutaceae) Bark*, Aust. J. Chem., 1989, 42, pp. 1375–1379.
Chihiro Ito et al., *New Carbazole Alkaloids from Murraya euchrestifolia Hayata*, Chem., Pharm. Bull, 38(6), 1990, vol. 38, No. 6, pp. 1548–1550.
Chemical Abstract, *Some reactions of coumestans*, vol. 84, 1976, p. 564.
Motoi Yogo et al., *Synthesis of Some Carbazolequinone Alkaloids and Their Analogues, Facile Palladium–Assisted Intramolecular Ring Closure of Arylamino–1,4–benzoquinones To Carbazole–1,4–quinones*, Chem. Pharm. Bull, 39(2), vol. 39, No. 2, pp. 328–334.
David Creed et al., *Photochemistry of Electron–Transport Quinones. II.$^1$ Model Studies with Plastoquinone–1 [2,3–Dimethyl–5–(3–methylbut–2–enyl)–1,4–benzoquinone]*, Journal of the American Chemical Society, 93(2), Jan. 27, 1971, pp. 502–511.
Asish DE, *Studies in Sulphur Heterocycles: Part III— Syntheses of Tricyclic Compounds with Condensed Thiophene Rings*, Indian Journal of Chemistry, vol. 23B, Oct. 1984, pp. 918–925.
Yun–Cheung Kong et al., *Micromelum: a Key Genus in the Chemosystematics of the Clauseneae*, Biochemical Systematics and Ecology, vol. 16, No. 5, 1988, pp. 485–489.

*Primary Examiner*—Philip Tucker
*Attorney, Agent, or Firm*—Burns, Doane, Swecker & Mathis, L.L.P.

[57] ABSTRACT

A spiro (indolino) oxazine compound of general formula (I)

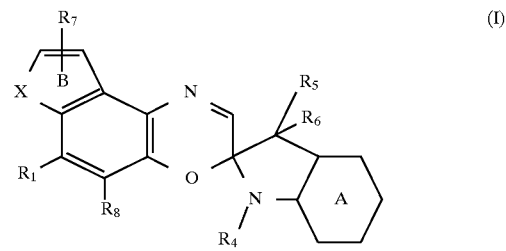

wherein $R_1$ represents a group of the formula —$NR_2R_3$ wherein each of $R_2$ and $R_3$, which may be the same or different, independently represents an alkyl group, or a carbocyclic group, preferably aryl, or a heterocyclic group, or $R_2$ and $R_3$ taken together with the nitrogen atom to which they are attached represent a heterocyclic ring having one or more heteroatoms and which may optionally carry at least one substituent selected from alkyl, aryl or heteroaryl groups;

—X— is selected from —O—, —S—, —Se—, —NH— or —NR— wherein R represents an alkyl group, and ring A is a carbocyclic or heterocyclic ring which can be optionally substituted with a group of formula $R_8$ as defined above, or may optionally have a carbocyclic or heterocyclic ring fused thereto; and wherein $R_4$–$R_8$ are as defined in the specification.

The spiro (indolino) oxazine compounds of the invention are useful as photochromic materials.

18 Claims, No Drawings

PHOTOCHROMIC COMPOUNDS

This application is a continuation of application Ser. No. 08/612,080, filed Mar. 7, 1996 now abandoned, which is a continuation of application Ser. No. 08/284,232, filed Aug. 2, 1994 now abandoned.

The present invention relates to certain novel photochromic spiro (indolino) oxazine compounds, and to articles and compositions containing them.

Photochromism is a well-known physical phenomenon which is observed with certain classes of chemical compounds. A detailed discussion of this phenomenon can be found in "Photochromism: Molecules and Systems", Studies in Organic Chemistry 40, Edited by H. Durr and H. Bouas-Laurent, Elsevier 1990.

Spiro oxazine compounds as a class of compounds are known to be capable of exhibiting a photochromic effect. For example, European Patent specification No. 0358774 describes a series of photochromic spiro oxazine compounds which are said to have an excellent resistance to fatigue and also provide a number of different colour hues.

U.S. Pat. No. 4,986,934 describes various spiro-benzoxazine pyrrolo pyridine compounds.

Our European Patent No. 0245020 describes a number of spiro-oxazine photochromic compounds all of which are characterised by the presence of an amine functionality at the 6'-position of the molecule. The compounds described in this patent specification are found to have an intense dark colouration in their darkened state.

We have now found a group of other spiro (indolino) oxazine compounds which also provide an intense dark colouration in their darkened state. One of the important characteristics of the novel spiro (indolino) compounds of the present invention is that they carry a substituted amino group in the 6'-position of the molecule.

Accordingly, the present invention provides a spiro (indolino) oxazine compound of general formula (I):

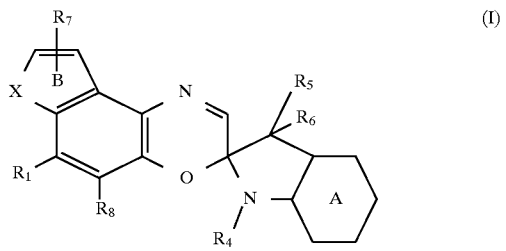

wherein $R_1$ represents a group of the formula $-NR_2R_3$ wherein each of $R_2$ and $R_3$, which may be the same or different, independently represents an alkyl group, or a carbocyclic group, preferably aryl, or a heterocyclic group, or $R_2$ and $R_3$ taken together with the nitrogen atom to which they are attached represent a heterocyclic ring having one or more heteroatoms and which may optionally carry at least one substituent selected from alkyl, aryl or heteroaryl groups;

$R_4$ represents an alkyl group which may be linear, branched or alicyclic;

each of $R_5$ and $R_6$, which may be the same or different, represents an alkyl group or a carbocyclic or heterocyclic group, or $R_5$ and $R_6$ taken together with the carbon atom to which they are attached represent a carbocyclic or heterocyclic ring which may optionally carry at least one substituent selected from alkyl, aryl or heteroaryl groups;

$R_7$ represents a hydrogen atom or an alkyl, aryl or heteroaryl group, or a carbocyclic or heterocyclic group which is fused to heterocyclic ring B;

$R_8$ represents a hydrogen atom or a substituent selected from alkyl, alkoxy, aryl, aryloxy, heteroaryl, halogen, azo, imino, amide, ester, cyano, trifluoromethyl or nitro group, or a dialkylamino group;

$-X-$ is selected from $-O-$, $-S-$, $-Se-$, $-NH-$ or $-NR-$ wherein R represents an alkyl group, and ring A is a carbocyclic or heterocyclic ring which can be optionally substituted with a group of formula $R_8$ as defined above, or may optionally have a carbocyclic or heterocyclic ring fused thereto.

For the avoidance of doubt, throughout this specification, the ring numbering system used to describe the spiro-oxazine compounds of the present invention is as follows:

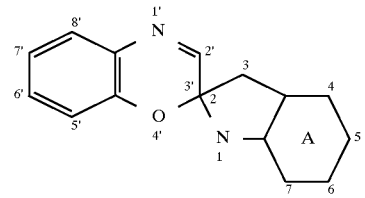

The spiro (indolino) oxazine compounds of the present invention exhibit very dark colouration (typically red, but also including other colours up to blue) in the darkened condition when compared with the colouration obtained with the corresponding materials which have no amino substituent in the 6'-position of the molecule.

The photochromic materials of the present invention which give a red colouration in the darkened state are particularly useful for mixing with complimentary spiro-oxazine compounds which exhibit a green colouration in their darkened condition. Typical compounds which give this green colouration are described in our U.K. patent application No. 9225346. By mixing the present compounds with such green photochromic compounds one can obtain a composite mixture of photochromic compounds which produces a neutral or grey colouration in the darkened state; this can be useful for certain tinted lenses, e.g. in sunglasses.

A further advantage of the photochromic materials of the present invention is that they are extremely efficient absorbers of long wave U.V. radiation (340–400 nm: UVa radiation) and are therefore very sensitive to actinic radiation. This means that these materials provide additional protection against UV irradiation.

Preferred spiro-oxazines in accordance with the invention are compounds of general formula (I) in which $-X-$ is $-O-$ (so as to form a furan ring), the group $R_7$ is a benzene ring fused to the said furan ring, and $R_8$ is a hydrogen atom, i.e. a compound of general formula (II):

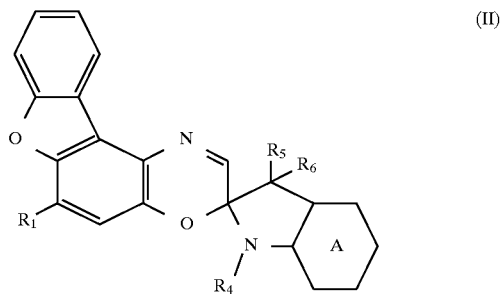

wherein $R_1$, $R_4$, $R_5$, $R_6$ and Ring A are as defined above.

Preferably ring A is a benzene ring or a benzene ring carrying an alkoxy group (usually a methoxy group) in the 5-position; or a pyridine ring with the nitrogen atom in the 7-position, optionally substituted with a single $CF_3$- group in the 5- or 6-position or substituted with two $CF_3$- groups in the 4- and 6-positions of the ring; or a pyrazine ring with nitrogen atoms in both the 4- and 7- positions of the ring.

Throughout this specification, unless stated otherwise, the term "alkyl" is to be taken to mean an alkyl group having from 1 to 4 carbon atoms. Similarly, the term "alkoxy" is to be taken to mean an alkoxy group having from 1 to 4 carbon atoms.

Furthermore, in the definitions given above for $R_1$, $R_5$, $R_6$ and $R_7$, whenever reference has been made to a carbocyclic or heterocyclic ring (or group), unless specified otherwise it is to be understood that such carbocyclic or heterocyclic rings (or groups) may be unsubstituted or may carry one or more substituents chosen from halogen atoms, alkyl, alkoxy, aryl, aryloxy, heteroaryl, amino, substituted amino, azo, imino, amide, carboxylate, ester, cyano, trifluoromethyl or nitro groups, or, further, such rings may have one or more further rings which are fused thereto.

For the avoidance of doubt, in the definition of $R_1$ above, the group —$NR_2R_3$ includes within its scope ring systems in which one or more further rings are fused to the heterocyclic ring, and such ring systems may incorporate saturated and/or unsaturated rings.

Preferably, the $R_1$ substituent is a piperidino group or a morpholino group.

Preferably, the $R_4$-substituent is a $C_{1-8}$ alkyl group, typically a methyl group, an isobutyl group or a neopentyl group.

Each of the $R_5$ and $R_6$ substituents is preferably a $C_{1-8}$ alkyl group, typically a methyl group, an isobutyl group or a neopentyl group, or the $R_5$ and $R_6$ groups together with the carbon atom to which they are attached preferably represent a spirohexyl group.

According to a further aspect of the present invention, there is provided a process for preparing a spiro (indolino) oxazine compound of general formula (I), which process comprises (a) oxidising a compound of general formula (II)

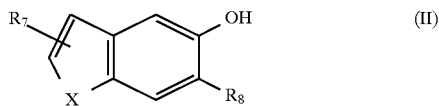

wherein X, $R_7$ and $R_8$ are as defined above, by use of oxygen in the presence of a complex of a copper (II) salt and an amine of formula $R_1H$ to yield a compound of formula (III)

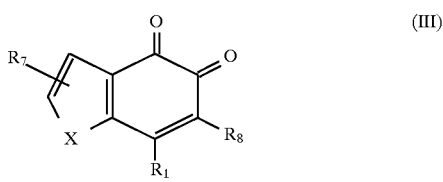

wherein X, $R_1$, $R_7$ and $R_8$ are as defined above, (b) heating the compound of formula (III) with hydroxylamine hydrochloride under reflux to yield a nitroso-hydroxy compound of formula (IV)

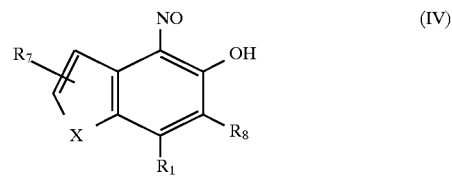

wherein X, $R_1$, $R_7$ and $R_8$ are as defined above, and (c) condensing the nitroso-hydroxy compound of formula (IV) with a 2-alkylidene indole compound of formula (V)

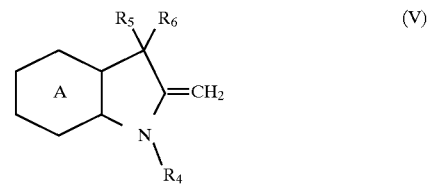

wherein $R_4$, $R_5$, $R_6$ and ring A are as defined above.

The novel spiro (indolino) oxazine compounds of the present invention are found to be particularly useful as photochromic materials to be incorporated into polymeric host materials so as to impart photochromic properties to the said polymeric host materials.

The photochromic compounds of the present invention are incorporated into the plastics host material in known manner, for example as described in European Patent No. 0245020 or U.S. Pat. No. 5,066,818.

The spiro-oxazine compounds of the invention exhibit substantially greater induced optical density (IOD) than prior art materials of comparable structure. As a result, the amount of photochromic material required to impart a useful degree of photochromism to a polymeric host material or to a solution is greatly reduced when compared to the amount required to obtain an equivalent photochromic effect with prior art photochromic materials.

The use of reduced quantities of the photochromic materials of the invention not only gives a saving in cost, but also has the added advantage that there is a consequent reduction in any undesirable colour that the photochromic materials may impart in the bleached state, either by way of the inherent colour of the photochromic material itself, or by way of any coloured degradation/fatigue products that may be generated during use of the photochromic material.

The colour range of the spiro (indolino) oxazine compounds of the present invention is 490 to 610 nm; thus, the materials of the present invention impart a red or purple or blue colouration in their darkened state. In the faded or bleached condition the materials exhibit a colourless or pale colouration.

Typical polymeric host materials are optically clear polymer materials, such as polymers of polyol(allyl carbonate)-monomers, polyacrylates such as polymethylmethacrylates, cellulose acetate, cellulose triacetate, cellulose acetate propionate, cellulose acetate butyrate, poly(vinyl acetate), poly(vinyl alcohol), polyurethanes, polycarbonates, polyethylene terephthalate, polystyrene, styrene/methylmethacrylate copolymers, styrene/acrylonitrile copolymers, and polyvinylbutyral. Transparent copolymers and blends of the transparent polymers are also suitable as host materials. Polymers of the type described in EP 0294056 or EP 0453149 are also suitable.

Preferably, the polymeric host material is an optically clear polymerized organic material such as a polyurethane or a polymer of diethylene glycol bis(allyl carbonate) (sold under the trade name CR-39), or SPECTRALITE—a material sold by Sola Optical USA.

Usually, the amount of photochromic spiro oxazine compound incorporated in the polymeric host material ranges from 0.001 to 0.5 wt %, based on the weight of the polymeric host material.

In some applications, it may be desirable or advantageous to combine the spiro oxazine compounds of the present invention with other photochromic materials to obtain an aggregate colour effect. For example, other known spiro-oxazine materials may have a colour range of 530 to 680 nm which means that in the darkened condition the spiro-oxazines impart a red-purple or purple or blue or blue-green or green colouration to a host material. Thus, the present spiro-oxazine compounds are complementary to known spiro-oxazine materials such as those described in our European Patent No. 0245020, or in our UK Patent Applications Nos. 92/25346, 92/25347 and 92/25348, or to the spiro (indolino) naphthoxazines, spire (indolino) pyrido benzoxazines and spiro (indolino) benzoxazines described in U.S. Pat. Nos. 4,637,698, 3,562,172, 3,578,602, 4,816,584, 4,215,010 and 4,342,668, and can be combined with such other photochromic materials. The compounds of the present invention may also be combined with other photochromic materials such as the naphthopyran compounds described in our U.K. Patent Application No. 9306587 or in U.S. Pat. No. 5,066,818.

Typically, when used in combination, the further additional photochromic material is present in an amount of from 0.001 to 0.5 weight %, based on the weight of the polymeric host material.

Examples of suitable uses of the photochromic plastic articles incorporating the spiro-oxazine compounds of the invention are in the manufacture of plano lenses, e.g. for sunglasses, and ophthalmic lenses and as photochromic transparencies for vehicles such as cars and aircraft.

The spirooxazine materials of the present invention may be prepared by a general preparative method which is based on the following reaction scheme:

SCHEME A

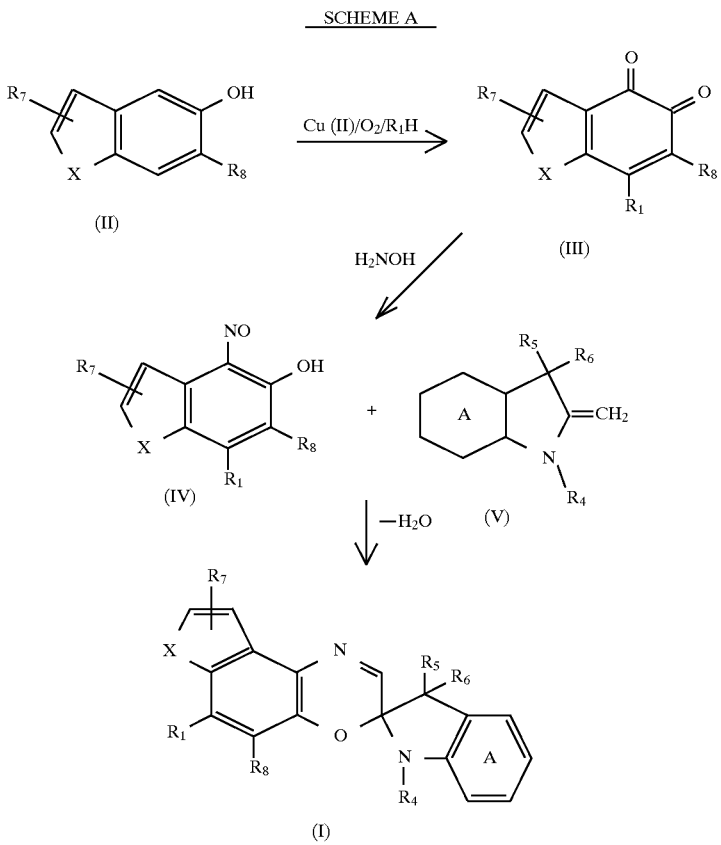

In reaction scheme A, an appropriately substituted 4-amino-1-nitroso-2-hydroxy compound (IV) is condensed with an appropriately substituted 2-alkylidene indole compound (V)—also referred to hereinbelow as a Fischer base analogue—to produce the spiro (indolino) oxazine compounds (I) of the present invention. This condensation reaction is analogous to the condensation reaction between nitrosonaphthols and 2-alkylidene indoles described in detail in, for example, "Photochromism: Molecules and Systems", edited by H. Durr and H. Bouas-Laurent, Studies in Organic Chemistry 40, Elsevier, 1990—see Chapter 10, and also in various patents such as EP 0245020 and U.S. Pat. No. 4,986,934.

The starting materials of formula (III) in reaction scheme A are believed to be new. The synthesis of these starting materials is based on the work of W. Brackman and E. Havinga, Recueil, 1955, 74, 937, 1021, 1071 and 1101. Their work details the synthesis of 4-amino-1,2-naphthaquinone from the readily available 2-naphthol. The initial reaction is the oxidation of the naphthol by gaseous oxygen and a catalytic quantity of copper (II) salt-amine complex (the complex is formed in situ by the simple addition of the copper (II) salt to the amine solution). The naphthoquinone formed in situ immediately reacts with the amine to form the amino naphthenediol which itself is immediately oxidised to form an amino-naphthoquinone product in good yield.

By analogy, the compounds of formula (III) are made using the same reaction sequence, as illustrated in Scheme B.

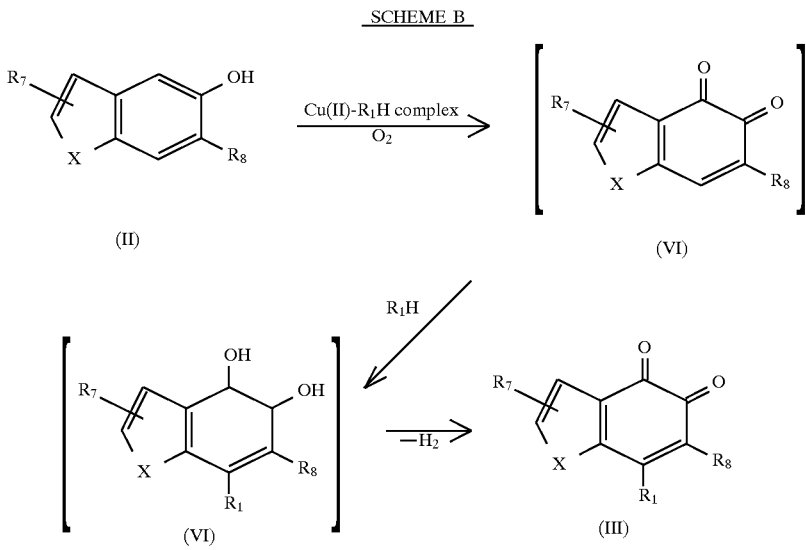

SCHEME B

By heating the compound of formula (III) with hydroxylamine hydrochloride under reflux, one obtains the compounds of formula (IV).

The starting materials of formula (V), i.e. the Fischer base analogues, are made by different methods, depending on the complexity of their structures. The synthesis of the simpler Fischer base analogues is well known and reported in the literature, see, for example, B. Robinson, The Fischer Indole Synthesis, Wiley-Interscience, 1982. Preparation of Fischer base analogues having a more complex structure, e.g. having N-branched alkyl substituents (e.g. N-neopentyl) or having a ring A which is-heterocyclic, is described in more detail in our U.K. Patent Application No. 9225347 or in Comprehensive Heterocyclic Chemistry, edited by A. R. Katritzky and C. W. Rees, Pergamon 1984, Vol 3, chapter 3.09, p. 497 et. seq. and in the papers by G. E. Ficken and J. D. Kendall, in J. Chem. Soc, 1959, 3203 and J. Chem. Soc., 1961, 584.

The following Examples illustrate the present invention. The structures of the various products were determined using n.m.r. and i.r. spectra.

EXAMPLE 1

1,3,3-Trimethyl-6'-piperidinospiro[2H-indole 2,3'-[3H]-[2H-[1,4]benzoxazino[6,5-b]benzofuran]].

Oxygen was bubbled, at a fast rate, for 3 hours, through a vigourously stirred solution of 2-hydroxydibenzofuran (73.8 g; 0.40 mol), copper (II) acetate (4.60 g; 0.025 mol) and piperidine (79.9 g; 0.94 mol) in methanol (600 ml) at room temperature. The resulting dark reaction mixture was filtered and the collected solid dried in air to give 4-piperidinodibenzofuran-1,2-dione as a very dark blue solid (66.3 g; 59%), m.pt. 151°–6° C.

4-Piperidinodibenzofuran-1,2-dione (18.4; 0.062 mol) was added in one portion to a vigorously stirred solution of hydroxylamine hydrochloride (22.9 g; 0.33 mol) and piperidine (28 g; 0.33 mol) in methanol (230 ml) at room temperature. After 1.75 hours the mixture was filtered and the resulting solid washed with water and dried to yield 2-hydroxy-1-nitroso-4-piperidinodibenzofuran as a red-brown solid (3.48 g; 19%), m.pt. 181°–185° C. (decomp 207° C.).

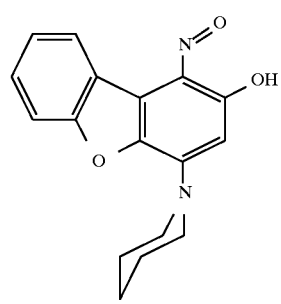

A mixture of 1,3,3-trimethyl-2-methyleneindoline (0.435 g; 0.0025 mol) and 2-hydroxy-1-nitroso-4- piperidinodibenzofuran (0.675 g; 0.0025 mol) in methanol (25.0 ml) was heated under nitrogen and refluxed with stirring for 41 hours. The solution was evaporated to dryness and chromatographed over silica (eluent: dichloromethane) to yield 1,3,3-trimethyl-6'-piperidinospiro[2H-indole 2,3'-[3H]-[2H-[1,4]benzoxazino [6,5-b]benzofuran]] as an amber oil (0.35 g; 32%), which afforded a pale yellow solid upon trituration with diethyl ether, m.pt. 213.5°–216° C.; $\lambda_{max}$ Absorbance 570 nm (Polyurethane).

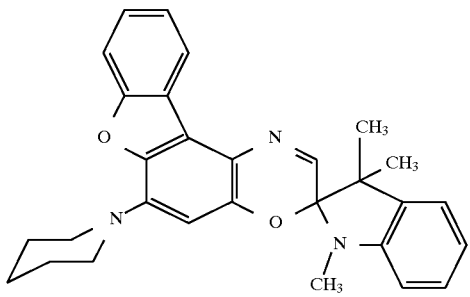

EXAMPLE 2

5-Trifluoromethyl-1,3,3-trimethyl-6'-piperidinospiro [2H-pyrrolo [2,3-b]pyridine-2,3'-[3H]-[2H-[1,4] benzoxazino[6,5-b]benzofuran]].

(a) 2-Chloro-5-trifluoromethylpyridine (44.3 g; 0.24 mol) was treated with several portions of methyl hydrazine (33.9 g; 0.74 mol) at room temperature under nitrogen. The mixture was heated at 90° C. for 6 hr. The resulting solid was treated with 3M aqueous NaOH and extracted with ethyl acetate. The organic extracts were dried and evaporated to leave an oil/solid. Distillation of the crude product to remove excess hydrazine gave 1-[5-trifluoromethylpyrid-2-yl]-1-methyl hydrazine as a white solid (44.0 g; 94%), m.pt. 52°–55° C.

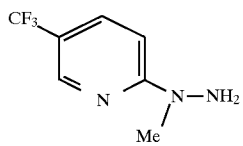

(b) A solution of 1-[5-trifluoromethylpyrid-2-yl]-1-methyl hydrazine (5.9 g; 0.031 mol), 3-methyl-2-butanone (5.6 g; 0.065 mol) and p-toluenesulphonic acid (0.1 g) in xylene (30 ml) was heated under reflux, with water removal (azeotrope), for 7 h. The solution was concentrated to yield an oil which was purified by distillation (70° C./72 mbar) to yield 3-methyl-2-butanone 1-[5-trifluoromethylpyrid-2-yl]-1-methyl hydrazone as a yellow oil (5.8 g; 72%).

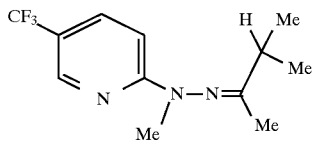

(c) 3-Methyl-2-butanone 1-[5-trifluoromethylpyrid-2-yl]-1-methyl hydrazone (49.5 g; 0.19 mol) was heated to 250° C. for 3 h. to yield a dark oil. Purification by flash-chromatography over silica (eluent: petroleum ether 60.80) afforded 5-trifluoromethyl-1,3,3-trimethyl-2-methylenepyrrolo [2,3-b]pyridine as an orange oil (11.0 g; 24%).

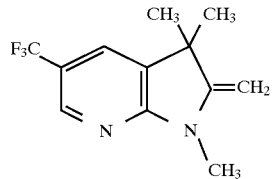

(d) A mixture of 5-fluoromethyl-1,3,3-trimethyl-2-methylenepyrrolo[2,3-b]pyridine (17.80 g; 0.074 mol) and 2-hydroxy-1-nitroso-4-piperidinodibenzofuran (24.1 g; 0.081 mol) in xylene (50 ml) was stirred and heated under nitrogen and refluxed for 24 hours. The solution was evaporated to dryness and the resulting gum chromatographed over silica (eluent: 5% diethyl ether in hexane) to give 5-trifluoromethyl-1,3,3-trimethyl-6'-piperidinospiro[2H-pyrrolo[2,3-b]pyridine-2,3'-[3H]-[2H-[1,4]benzoxazino[6, 5-b]benzofuran]] as a red gum which afforded a pale yellow solid (2.35 g; 6.1%) after trituration with hexane, m.pt. 254°–6° C., $\lambda_{max}$ Absorbance 506 nm (polyurethane).

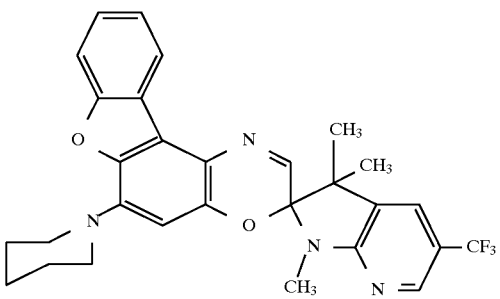

EXAMPLES 3 to 5

Using preparative procedures analogous to that described in Example 1, the following spiro (indolino) oxazines in accordance with the invention were also prepared:

EXAMPLE 3

5-Methoxy-1,3,3-trimethyl-6'-piperidinospiro[2H-indole 2,3'-[3H]-[2H-[4]benzoxazino[6,5-b] benzofuran]]

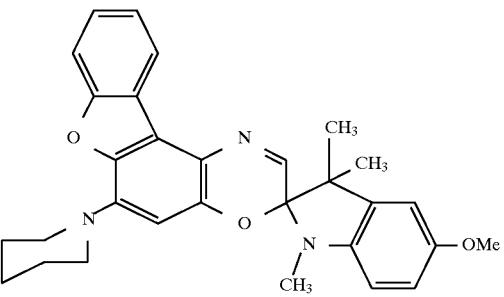

The structure of this compound was elucidated using spectroscopic methods (n.m.r. and i.r.). It had a m.pt. of 194°–200° C., and $\lambda_{max}$ absorbance of 598 nm (polyurethane).

EXAMPLE 4

1,3,3-Trimethyl-6'-piperidinospiro[2H-pyrrolo[2,3-b]
pyrazine-6,3'-[3H]-[2H-[1,4]benzoxazino[6,5-b]
benzofuran]]

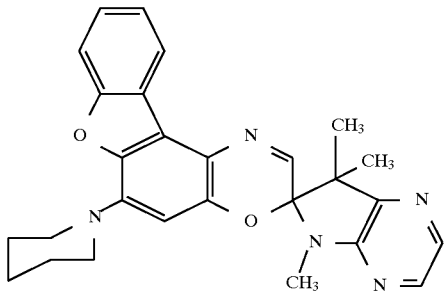

The structure of this compound was elucidated using spectroscopic methods (n.m.r. and i.r.). It had a m.pt. of 151°–161° C., and $\lambda_{max}$ absorbance of 510 nm (polyurethane).

EXAMPLE 5

3,3-Dimethyl-1-neopentyl-6'-pipidinospiro[2H-indole 2,3'-[3H]-[2H-[1,4]benzoxazino[6,5-b]
benzofuran]]

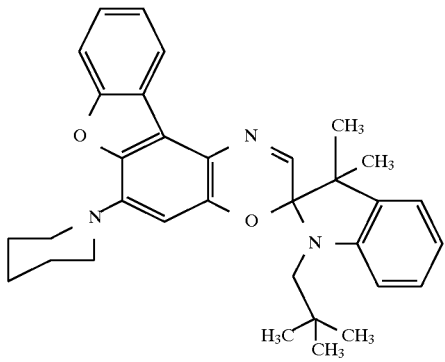

The structure of this compound was elucidated using spectroscopic methods (n.m.r. and i.r.). It had a m.pt. of 167°–173° C., and $\lambda_{max}$ absorbance of 588 nm (polyurethane).

EXAMPLE 6

6-Trifluoromethyl-1,3,3-trimethyl-6'-piperidinospiro
[2H-pyrrolo [2,3-b]pyridine-2,3'-[3H]-[2H-[1,4]
benzoxazino[6,5-b]benzofuran]]

(a) 2-Chloro-6-trifluoromethylpyridine (29.28 g; 0.16 mol) was treated with several portions of methyl hydrazine (7.9 g; 0.17 mol) and stirred under nitrogen at room temperature for 24 h. The mixture was treated with 5M aqueous NaOH to basify (pHil) and extracted with ethyl acetate. The organic extracts were dried and evaporated to leave an oil (30.12 g) which was flash-chromatographed over silica (eluent: 33% diethyl ether in hexane) to afford 1-[6-trifluoromethylpyrid-2-yl]-1-methyl hydrazine as a yellow oil (12.12 g; 38%).

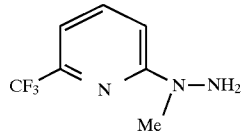

(b) A solution of 1-[6-trifluoromethylpyrid-2-yl]-1-methyl hydrazine (12.12 g; 0.069 mol), 3-methyl-2-butanone (5.96 g; 0.069 mol) and p-toluenesulphonic acid (0.13 g) in toluene (70 ml) was heated under reflux, with water removal (azeotrope), for 24 h. The solution was concentrated to yield an oil which was purified by flash-chromatography over silica (eluent: 20% diethyl ether in hexane) to yield 3-methyl-2-butanone 1-[6-trifluoromethylpyrid-2-yl]-1-methyl hydrazone as an orange oil (11.6 g; 71%).

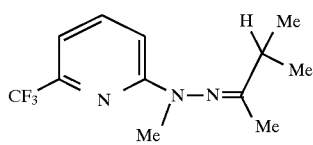

(c) 3-Methyl-2-butanone 1-[6-trifluoromethylpyrid-2-yl]-1-methyl hydrazone (11.45 g; 0.044 mol) was heated to 250° C. for 15 h. to yield a dark oil/gum. Flash-chromatography over silica (eluent: 20% diethyl ether in petroleum ether 60.80) afforded 6-trifluoromethyl-1,3,3-trimethyl-2-methylenepyrrolo[2,3-b]pyridine as a dark orange oil (6.2 g;58%).

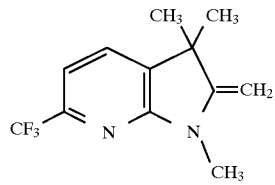

(d) A mixture of 6-trifluoromethyl-1,3,3-trimethyl-2-methylenepyrrolo[2,3-b]pyridine (1.45 g; 0.006 mol) and 2-hydroxy-1-nitroso-4-piperidinodibenzofuran (2.0 g; 0.0066 mol) in xylene (60 ml) was stirred and heated under nitrogen and refluxed for 24 hours. The solution was evaporated to dryness and the resulting gum chromatographed over silica (eluent: 20% diethyl ether in hexane) to give 6-trifluoromethyll-1,3,3-trimethyl-6'-piperidinospiro[2H-pyrrolo[2,3-b]pyridine-2,3'-[3H]-[2H-[1,4]benzoxazino[6,5-b]benzofuran]] as an orange solid (0.13 g; 4%), m.pt. 221°–5° C., $\lambda_{max}$ absorbance 506 nm (polyurethane).

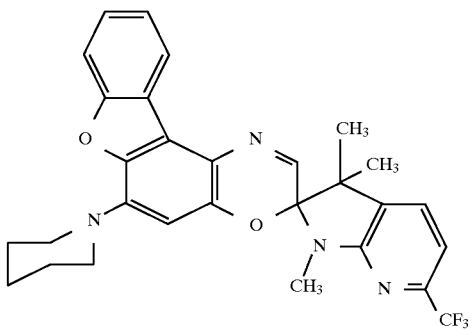

EXAMPLE 7

4,6-Bis(trifluoromethyl)-1,3,3-trimethyl-6'-pipidinospiro [2H-pyrrolo[2,3-b]pyridine-2,3'-[3H]-[2H-[1,4]benzoxazino[6,5-b]benzofuran]]

(a) 2-Chloro-4,6-bis(trifluoromethyl)pyridine (19.4 g; 0.078 mol) was treated with several portions of methyl hydrazine (4.2 g; 0.090 mol) and stirred under nitrogen at room temperature for 24 h. The oil/solid mixture was treated with 5M aqueous NaOH to basify (pHil) and extracted with ethyl acetate. The organic extracts were dried and evaporated to afford 1-[4,6-bis[trifluoromethyl]pyrid-2-yl]-1-methyl hydrazine as an oil (18.4 g; 91%).

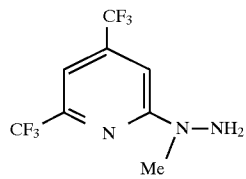

(b) A solution of 1-[4,6-bis[trifluoromethyl]pyrid-2-yl]-1-methyl hydrazine (40.04 g; 0.15 mol), 3-methyl-2-butanone (14.2 g; 0.165 mol) and p-toluenesulphonic acid (0.32 g) in toluene (90 ml) was heated under reflux, with water removal (azeotrope), for 40 h. The solution was concentrated to yield a dark oil which was purified by flash-chromatography over silica (eluent: petroleum ether 60/80) to yield 3-methyl-2-butanone 1-[4,6-bis[trifluoromethyl]pyrid-2-yl]-1-methyl hydrazone as a red oil (10.9 g; 22%).

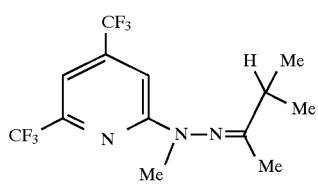

(c) 3-Methyl-2-butanone 1-[4,6-bis[trifluoromethyl]pyrid-2-yl]-1-methyl hydrazone (109 g; 0.033 mol) was heated to 245° C. for 15 h. to yield a dark oil. Flash-chromatography over silica (eluent: 4% diethyl ether in petroleum ether 60/80) afforded 4,6-bis[trifluoromethyl]1,3,3-trimethyl-2-methylenepyrrolo[2,3-b]pyridine as a low melting brown solid (3.3 g; 32%).

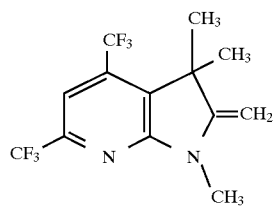

(d) A mixture of 4,6-bis[trifluoromethyl]-1,3,3-trimethyl-2-methylenepyrrolo[2,3-b]pyridine (1.83 g; 0.0059 mol) and 2-hydroxy-1-nitroso-4-piperidinodibenzofuran (2.60 g; 0.01 mol) in xylene (50 ml) was stirred and heated under nitrogen and refluxed for 24 hours. A further portion of 2-hydroxy-1-nitroso-4-piperidinodibenzofuran (1.2 g; 0.0059 mol) was added and the reaction continued for a further 24 h. The resulting dark solution was evaporated to dryness and the resulting gum chromatographed over silica (eluent: 2% diethyl ether in petroleum ether 60/80) to give 4,6-bis [trifluoromethyl]-1,3,3-trimethyl-6'-piperidinospiro[2H-pyrrolo[2,3-b]pyridine-2,3'-[3H]-[2H-[1,4]benzoxazino[6,5-b]benzofuran]] as an orange solid (0.08 g; 3%), m.pt. 195°–205° C., $\lambda_{max}$ absorbance 498 nm (polyurethane).

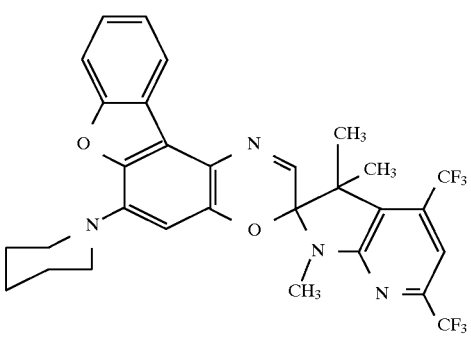

COMPARATIVE EXAMPLE 1

1,3,3-Trimethylspiro[2H-indole-2,31-3H-naphth[2,1-b][1,4]oxazine].

A mixture of 1,3,3-trimethyl-2-methyleneindoline (3.62 g; 0.021 mol) and 1-nitroso-naphthol (3.46 g; 0.02 mol) in ethanol (80.0 ml) was heated under reflux for 2 h. The solution was evaporated and the residue flash-chromatographed over silica (eluent: dichloromethane) to give 1,3,3-trimethylspiro[2H-indole-2,3'-3H-naphth[2,1-b][1,4]oxazine] as a pale yellow solid (3.96 g; 60%), m.pt. 127°–130° C.

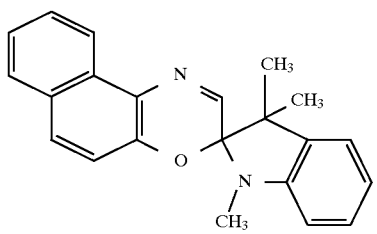

The photochromic properties of the spiro-indolino oxazine compounds of the present invention were tested by preparing, in conventional manner, by a direct casting process, 1.0 mm plates of a polyurethane host material of the type described in EP 0294056 incorporating the photochromic spiro-oxazine in a concentration of 0.25% w/w.

The resultant plates were illuminated under standard solar simulation conditions at Air Mass 2° at 21° C. (see Parry Moon, J. Franklin Inst. 230, (1940), p 583–617). The measurements which were made on the samples in the darkened condition were taken when the samples had reached a steady state; this steady state was deemed to have been reached after 10 minutes in the darkened condition.

The results obtained are set out in Table 1. The relatively high IOD values obtained with the spiro (indolino) oxazine compounds of the present invention (ranging from 0.34 to 1.08) demonstrate the dense colouring which is obtained with the photochromic materials of the present invention. These results contrast markedly with the low IOD values obtained with the comparative sample (0.27). A more proper comparison is between Example 1 (IOD of 0.61) and the Comparative Example (IOD of 0.27).

The photochromic compounds of the present invention are also found, in general, to exhibit good fatigue resistance, that is to say that the compounds of the present invention are found, in general, to be capable of maintaining their good photochro-mic properties and intense dark colouration in the darkened state over relatively long periods of time without undergoing any substantial degree of degradation.

TABLE 1

Comparative Test (0.25 w/w % in Polyurethane)

| | Bleached Transmission IVT | Darkened Transmission IVT | Induced Optical Darkening IVT | λmax nm |
|---|---|---|---|---|
| Example | | | | |
| 1 | 88.8 | 21.8 | 0.61 | 570 |
| 2 | 86.8 | 33.0 | 0.42 | 506 |
| 3 | 87.4 | 40.0 | 0.34 | 598 |
| 4 | 83.6 | 17.1 | 0.69 | 510 |
| 5 | 89.9 | 7.4 | 1.08 | 588 |
| 6 | 89.2 | 23.9 | 0.57 | 506 |
| Comparative Example | | | | |
| 1 | 88.7 | 47.9 | 0.27 | 605 |

We claim:
1. A spiro (indolino) oxazine compound of general formula I:

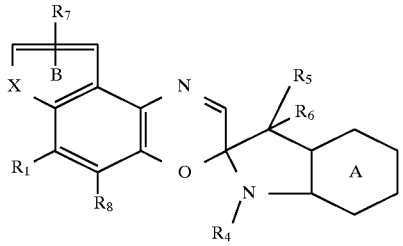

wherein $R_1$ represents a group of the formula $-NR_2R_3$ wherein each of $R_2$ and $R_3$, which may be the same or different, independently represents an alkyl group, or a carbocyclic group, or a heterocyclic group or $R_2$ and $R_3$ taken together with the nitrogen atom to which they are attached represent a heterocyclic ring including one or more heteroatoms and which may optionally carry at least one substituent selected from alkyl, aryl or heteroaryl groups and which optionally may have one or more farther carbocyclic rings fused thereto;

$R_4$ represents an alkyl group which may be linear, branched or alicyclic;

each of $R_5$ and $R_6$, which may be the same or different, represents an alkyl group or a carbocyclic group, or $R_5$ and $R_6$ taken together with the carbon atom to which they are attached represent a carbocyclic ring which may optionally carry at least one substituent selected from alky, aryl or heteroaryl groups;

$R_7$ represents a hydrogen atom or an alkyl, an aryl or a heteroaryl group, or a carbocyclic group which is fused to heterocyclic ring B;

$R_8$ represents a hydrogen atom or a substituent selected from alkyl, alkoxy, aryl, aryloxy, heteroaryll, halogen, azo, imino, amide, ester, cyano, trifluoromethyl or nitro group, or a dialkylamino group;

—X— is selected from —O—, —S—, —Se—, —NH— or —NR— wherein R represents an alkyl group, and ring A is a ring selected from carbocyclic, pyridine or pyrazine which can be optionally substituted with a group of formula $R_8$ as defined above, or may optionally have a carbocyclic ring fused thereto.

2. A spiro (indolino) oxazine compound according to claim 1, wherein —X— is —O— (so as to form a furan ring), the group $R_7$ is a benzene ring fused to the said furan ring, and $R_8$ is a hydrogen atom.

3. A spiro (indolino) oxazine compound according to claim 1, wherein $R_1$ is a piperidino or a morpholino group.

4. A spiro (indolino) oxazine compound according to claim 1, wherein $R_4$ is a $C_{1-8}$ alkyl group.

5. A spiro (indolino) oxazine compound according to claim 1, wherein each of $R_5$ and $R_6$ independently represents a $C_{1-8}$ alkyl group.

6. A spiro (indolino) oxazine compound according to claim 1, wherein $R_5$ and $R_6$ taken together with the carbon atom to which they are attached represent a spirohexyl group.

7. A spiro (indolino) oxazine compound according to claim 1, wherein ring A is a benzene ring or a benzene ring carrying an alkoxy group in the 5-position; or a pyridine ring with the nitrogen atom in the 7-position, optionally substituted with a single $CF_3$- group in the 5- or 6-position or substituted with two $CF_3$- groups in the 4- and 6-positions of the ring; or a pyrazine ring with nitrogen atoms in both the 4- and 7-positions of the ring.

8. A photochromic article comprising a polymeric host material having a spiro (indolino) oxazine compound as defined in claim 1 incorporated therein or applied thereto.

9. A photochromic article according to claim 8, wherein the polymeric host material is selected from polymers of polyol (allyl carbonate) monomers, polyacrylates, poly (alkylacrylates), cellulose acetate, cellulose triacetate, cellulose acetate propionate, cellulose acetate butyrate, poly (vinyl acetate), poly(vinyl alcohol), polyurethanes, polycarbonates, polyethylene terephthalate, polystyrene, styrene/methylmethacrylate copolymers, styrene/acrylonitrile copolymers, and polyvinylbutyral.

10. A photochromic article according to claim 9, wherein the polymeric host material is a polyurethane or a polymer of diethyleneglycol bis (allyl carbonate).

11. A photochromic article according to claim 8, wherein the amount of spiro (indolino) oxazine compound is from 0.001 to 0.5% by weight, based on the weight of the polymeric host material.

12. A photochromic article according to claim 8, comprising a further photochromic compound selected from spiro(indoline)naphthoxazines, spiro(indolino)pyrido benzoxazines, spiro(indolino)benzoxazines, and naphthopyrans.

13. A photochromic article according to claim 12, wherein the further photochromic compound is present in an amount of from 0.001 to 0.5% by weight, based on the weight of the polymeric host material.

14. A photochromic article according to claim 8, which is in the form of a lens.

15. A photochromic article according to claim 14, wherein the lens is an ophthalmic lens.

16. The compound of claim 1 which is 1,3,3-Trimethyl-6'-piperidinospiro[2H-indole 2,3'-[3H]-[2H-[1,4]benzoxazino[6,5-b]benzofuran]];

5-Trifluoromethyl-1,3,3-trimethyl-6'-piperidinospiro[2H-pyrrolo[2,3-b]pyridine-2,3'-[3H]-[2H-[1,4]benzoxazino[6,5-b]benzofuran]];

5-Methoxy-1,3,3-trimethyl-6'-piperidinospiro[2H-indole 2,3'-[3H]-[2H-[1,4]benzoxazino[6,5-b]benzofuran]];

1,3,3-Trimethyl-6'-piperidinospiro[2H-pyrrolo[2,3-b]pyrazine-6,3'-[3H]-[2H-[1,4]benzoxazino[6,5-b]benzofuran]];

3,3-Dimethyl-1-neopentyl-6'-pipidinospiro[2H-indole 2,3'-[3H]-[2H-[1,4]benzoxazino[6,5-b]benzofuran]];

6-Trifluoromethyl-1,3,3-trimethyl-6'-piperidinospiro[2H-pyrrolo[2,3-b]pyridine-2,3'-[3H]-[2H-[1,4]benzoxazino[6,5-b]benzofuran]]; or 4,6-Bis(trifluoromethyl)-1,3,3-trimethyl-6'-pipidinospiro[2H-pyrrolo[2,3-b]pyridine-2,3'-[3H]-[2H-[1,4]benzoxazino[6,5-b]benzofuran]].

17. A spiro (indolo) oxazine compound according to claim 4, wherein $R_4$ is selected from the group consisting of methyl, isobutyl or neopentyl.

18. A spiro (indolo) oxazine compound according to claim 5, wherein $R_5$ and $R_6$ are independently selected from the group consisting of methyl, isobutyl or neopentyl.

* * * * *